United States Patent
Basir et al.

(10) Patent No.: US 7,230,564 B2
(45) Date of Patent: Jun. 12, 2007

(54) MICROWAVE METHOD AND SYSTEM FOR MATERIAL INSPECTION

(75) Inventors: Otman Adam Basir, Waterloo (CA); Yang Yang, Sunnyvale, CA (US); Yaxun Liu, Markham (CA); Gauri S. Mittal, Guelph (CA)

(73) Assignee: 1M International Corporation, Waterloo (CA)

( * ) Notice: Subject to any disclaimer, the term of this patent is extended or adjusted under 35 U.S.C. 154(b) by 0 days.

(21) Appl. No.: 11/151,595

(22) Filed: Jun. 13, 2005

(65) Prior Publication Data

US 2005/0285772 A1    Dec. 29, 2005

Related U.S. Application Data

(60) Provisional application No. 60/578,955, filed on Jun. 11, 2004.

(51) Int. Cl.
  *G01S 13/88* (2006.01)
  *G01S 13/00* (2006.01)
  *G01S 7/00* (2006.01)

(52) U.S. Cl. .......................... 342/22; 342/27; 342/175; 342/195; 426/231; 426/232; 426/234; 426/237

(58) Field of Classification Search .................. 342/21, 342/22, 175, 188–197, 27, 28; 99/451; 426/231–234, 426/237–248
See application file for complete search history.

(56) References Cited

U.S. PATENT DOCUMENTS

| | | | |
|---|---|---|---|
| 3,351,936 A * | 11/1967 | Feder | 342/22 |
| 4,075,555 A * | 2/1978 | Wight et al. | 342/22 |
| 4,161,731 A * | 7/1979 | Barr | 342/22 |
| 5,446,461 A * | 8/1995 | Frazier | 342/22 |
| 5,900,833 A * | 5/1999 | Sunlin et al. | 342/22 |
| 5,912,639 A * | 6/1999 | Beckner | 342/22 |
| 5,920,285 A * | 7/1999 | Benjamin | 342/22 |
| 5,952,954 A * | 9/1999 | Beckner | 342/22 |
| 6,002,357 A * | 12/1999 | Redfern et al. | 342/22 |
| 6,091,354 A * | 7/2000 | Beckner et al. | 342/22 |
| 6,130,641 A * | 10/2000 | Kraeutner et al. | 342/22 |
| 6,429,802 B1* | 8/2002 | Roberts | 342/22 |
| 6,445,334 B1* | 9/2002 | Bradley et al. | 342/22 |
| 6,480,141 B1* | 11/2002 | Toth et al. | 342/22 |
| 6,496,137 B1* | 12/2002 | Johansson | 342/22 |
| 6,531,881 B1* | 3/2003 | Cordes et al. | 342/22 |
| 6,545,945 B2* | 4/2003 | Caulfield | 342/22 |
| 6,573,855 B1* | 6/2003 | Hayakawa et al. | 342/22 |
| 6,600,441 B2* | 7/2003 | Liedtke et al. | 342/22 |

* cited by examiner

*Primary Examiner*—Bernarr E. Gregory
(74) *Attorney, Agent, or Firm*—Carlson, Gaskey & Olds, PC

(57) ABSTRACT

A microwave system is capable of inspecting a medium, especially capable of inspecting food products transferred by a conveyer belt in real time. The microwave system includes a transmitter for transmitting continuous microwave; a receiver for receiving the microwave passing through the medium; a scanner for electrically directing a microwave beam along a linear path, especially, across the conveyer belt; a waveform extractor for extracting the informational parts of the received signal outputted by the receiver; and a cpu for analyzing the data outputted by waveform extracting means.

10 Claims, 6 Drawing Sheets

MICROWAVE METHOD AND SYSTEM FOR MATERIAL INSPECTION

This application claims priority to U.S. Provisional Application Ser. No. 60/578,955 filed Jun. 11, 2004.

BACKGROUND OF THE INVENTION

Medium inspection plays an important role in medical imaging, non-destructive evaluation and remote sensing. Ultrasonic based systems and X-ray based systems are widely used for material inspection. The inspection methods based on ultrasound use high frequency sound waves to detect and image features of a material. Pulsed beams of ultrasound can be produced with a transducer. Any sound that returns to the transducer gives two main measurements: amplitude of returned signal and time elapsed between emission and reception by the transducer. A common limitation of sonic systems is the poor resolution, which is caused by the low operation frequencies. X-ray system is a precise and efficient way to inspect the material. However, there are several limitations in this technology: i) the price of the X-ray system is expensive; and ii) X-ray exposure of the operators must be limited.

Similar to X-ray, microwave can "see through" the target. The technique utilizing the property has being developed very fast recently. This technique is efficient, can provide high resolution images for the target medium by making use of the reflection, scattering, diffraction and attenuation properties of electromagnetic fields. In addition, the generation and control of microwave are easier compared with X-ray, ultrasonic and other imaging technologies. Furthermore, with the development of wireless communications, the components required in the microwave system are inexpensive.

BRIEF SUMMARY OF THE INVENTION

A microwave inspection system according to the present invention inspects the features of the target material using two waveguide arrays for microwave transmission and reception. Two switches are connected to waveguide arrays for controlling each waveguide to transmit or receive the signals. The scattered signals are collected by a scanning scheme. The magnitude and phase information is extracted from coherent signals.

The present microwave system can detect a contaminant in the target medium. Furthermore with this equipment, the complete image may be obtained.

BRIEF DESCRIPTION OF THE DRAWINGS

Other advantages of the present invention can be understood by reference to the following detailed description when considered in connection with the accompanying drawings wherein.

DETAILED DESCRIPTION OF THE INVENTION

Figure 1:
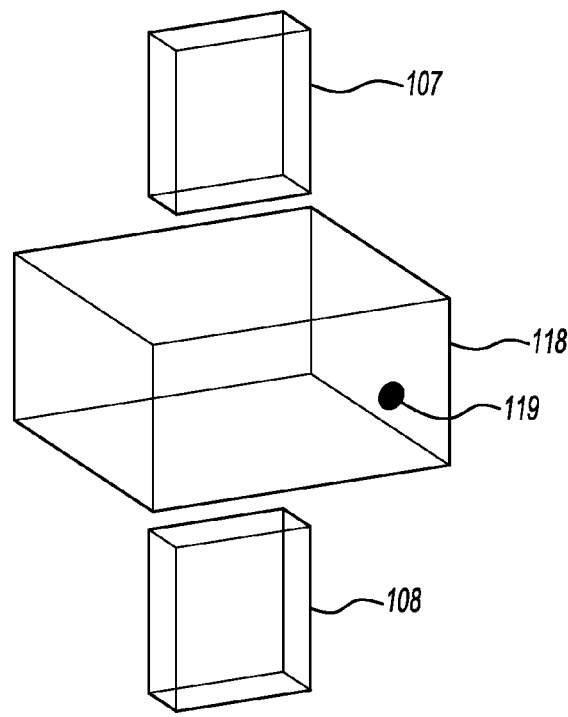
FIG. 1 illustrates basic microwave transmission system according to the present invention.

A microwave inspection system 10 according to the present invention utilizes the properties of a basis microwave transmission system as shown in FIG. 1. The top waveguide 107 is connected to microwave transmitter and the bottom waveguide 108 is connected to receiver. Assuming microwave is transmitted from the top waveguide 107 toward bottom waveguide 108, part of microwave will enter the bottom waveguide 108 with attenuation and phase delay, which depends on the medium between the two waveguides 107, 108 and is represented by the parameter $S_{21}$. Therefore by observing the variation of $S_{21}$ it is possible to detect the variation of medium 118. If there is anomaly such as metal or heterogeneous dielectric object 119 in the medium 118, it will also affect $S_{21}$, and the effect is localized, therefore it is possible to detect the anomaly by scanning the medium 118 for measuring $S_{21}$.

Accurate prediction of the interactions between the waveguides 107, 108, the medium 118 and the object 119 requires solution of Maxwell's equations [assuming time dependence of $\exp(j\omega t)$]

$$\nabla \times \vec{E} = -j\omega\mu\vec{H} \quad (1)$$

$$\nabla \times \vec{H} = \vec{J} + \omega \in \vec{E} \quad (2)$$

where $\in$ and $\mu$ are permittivity and permeability of materials which are functions of position. The boundary conditions are $$\hat{n} \times \vec{E} = 0, \text{ on PEC surface} \quad (3)$$

$$\hat{n} \times (\vec{E}_1 - \vec{E}_2) = 0, \text{ on dielectric interface} \quad (4)$$

$$\hat{n} \times (\vec{H}_1 - \vec{H}_2) = 0, \text{ on dielectric interface} \quad (5)$$

where $\hat{n}$ is the normal vector of the surface, $\vec{E}_1$ and $\vec{E}_2$ denotes electric fields on the two sides of the interface.

Accurate solution of Maxwell's equations requires numerical methods such as Finite Element Method (FEM), Method of Moments (MoM) or Finite-Difference Time-Domain (FDTD) method, for which there is commercial software such as Ansoft HFSS (FEM) or Zeland Fidelity (FDTD) available. There has been no simple formula for accurately calculating $S_{21}$ of configuration shown in FIG. 1 with or without anomaly, however, the Radar Equation may be used for rough estimation of power level or gaining some intuition of the interaction, which is $$\frac{W'}{W} = \frac{GG'\lambda^2 \sigma}{(4\pi)^3 r_1^2 r_2^2} \quad (6)$$

where W' is the received power, W is the transmitted power, G and G' are the gains of the transmitting and receiving antennas, respectively, λ is the wavelength of the microwave, $r_1$ and $r_2$ are the distances from the scatterer to the transmitting and receiving antennas, respectively, σ is the radar cross section (RCS) of the scatterer which depends on the size, shape and material of the scatterer and also is a function of the incidence direction and observing direction.

Figure 2:
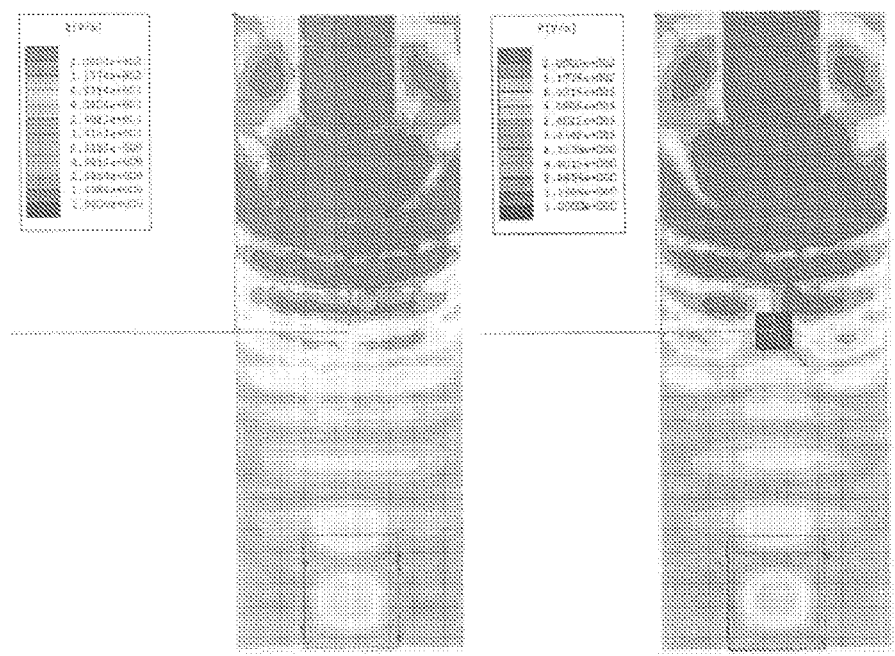
FIG. 2 illustrates a simulated electric field with (a) and without (b) PEC object.
Figure 4:
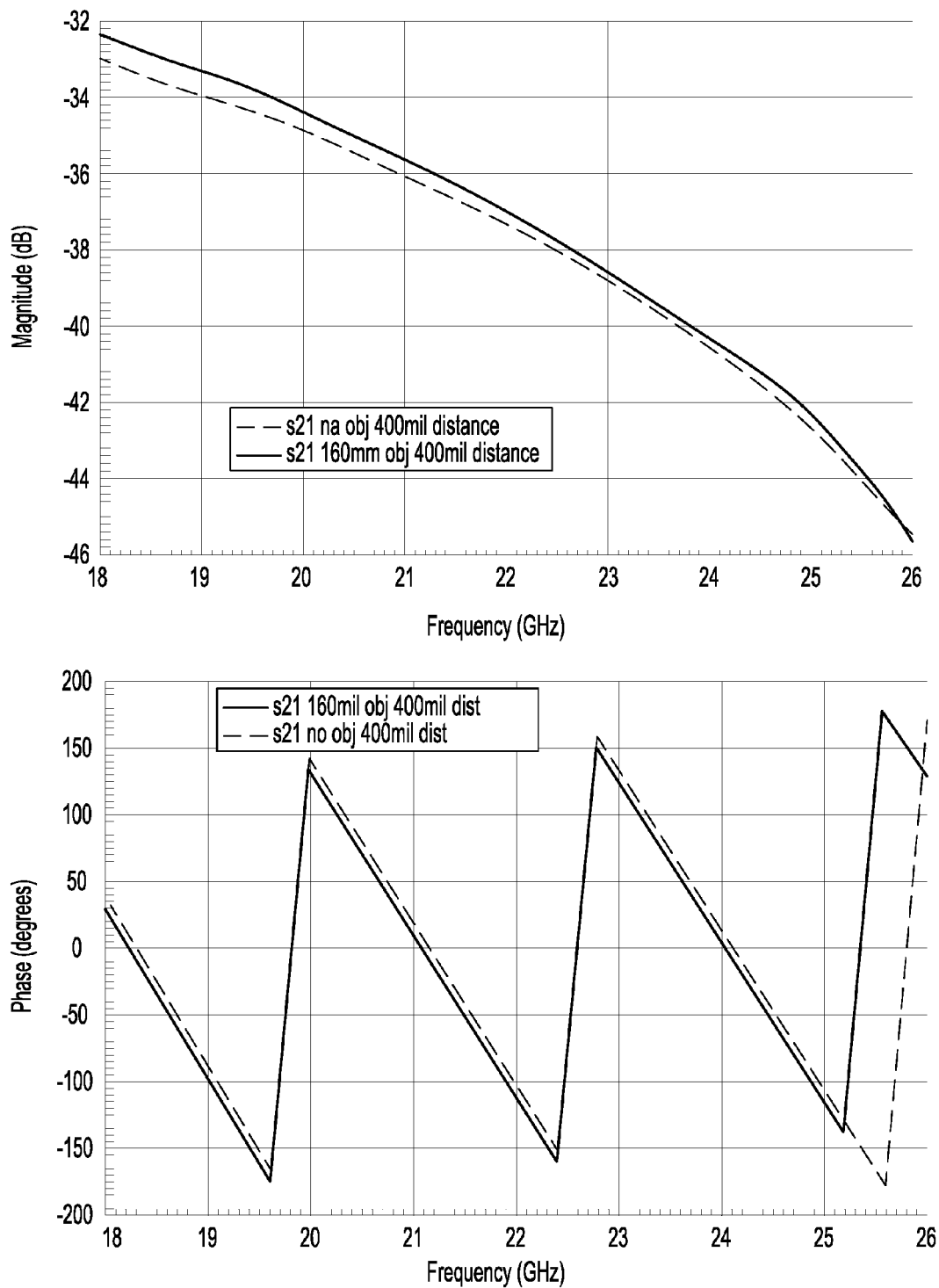
FIG. 4 illustrates the magnitude and phase change for the microwave system of FIG. 1.

FIG. 2 shows the simulation result of electric field with and without a PEC (perfect electrically conductive) object 119 in a cereal block using HFSS. From this figure we can see due to the disturbance of the PEC object 119, there is a phase delay for the wave entering the bottom waveguide compared with the case when there is no PEC object 119. FIG. 4 shows the simulated S-parameter, from which we can see the PEC object 119 caused variations of both amplitude and phase of $S_{21}$.

Figure 5:
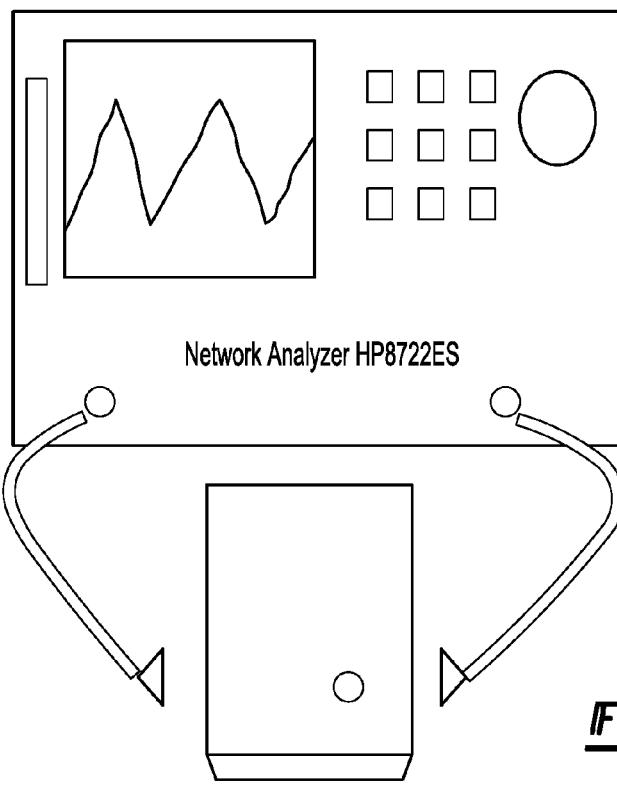
FIG. 5 schematically illustrates one potential experimental setup using VNA (for cereal box testing).
Figure 6A:
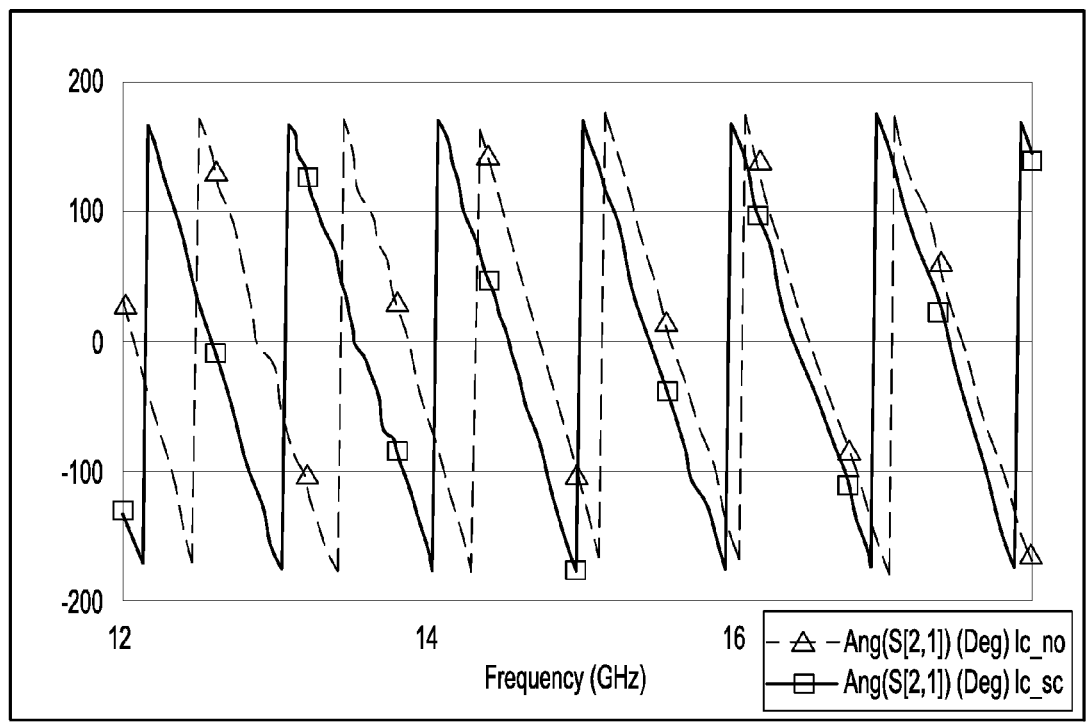
FIG. 6(a) shows the phase difference (no-object VS screw for cereal box 1 testing).
Figure 6B:
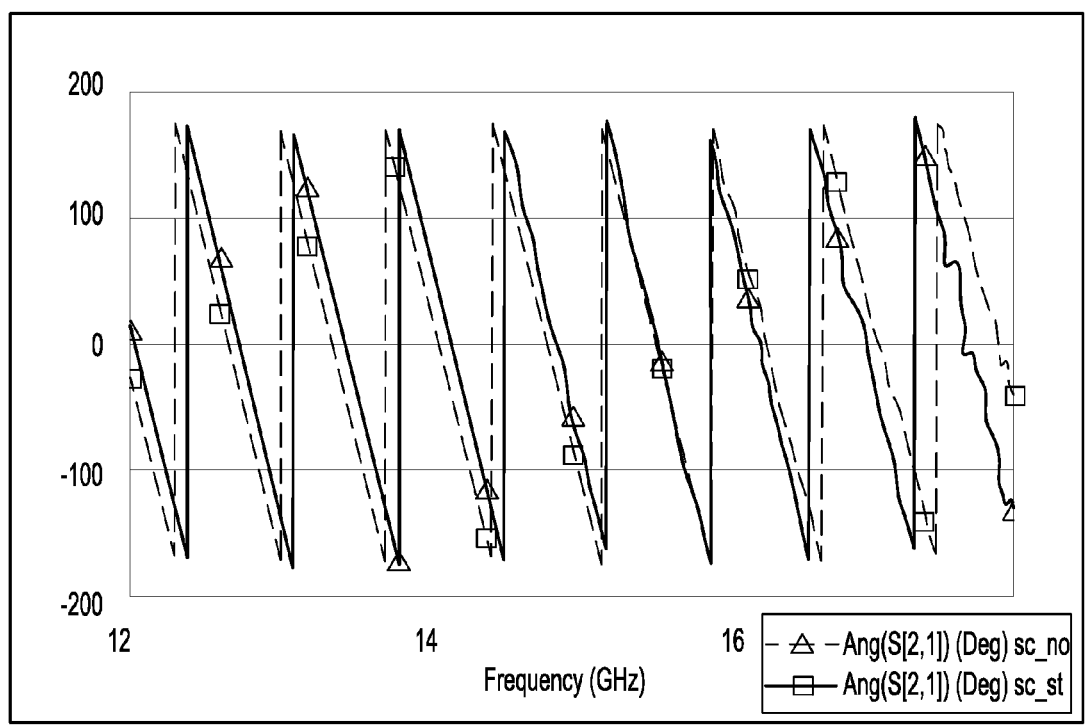
FIG. 6(b) shows the phase difference (no-object VS stone for cereal box 2 testing).

To verify the design concept and simulation results, preliminary experiments have been carried out. The network analyzer HP8722ES was working as our system, i.e. the transmitter and receiver. In addition, two waveguides are used. The measurement configuration is shown in FIG. 5. The phase character of the S parameter was measured and shown in FIG. 6. The results are similar to the simulated ones. The observations show that there is obvious phase difference for two conditions, with and without object 119. The experimental conditions are illustrated below.

TABLE 3.1

Experimental conditions using VNA

| | |
|---|---|
| Scan frequency band | 12–18 GHz |
| Transmission power | 10 dBm |
| Cereal box 1 | 22*16.5*5 cm(Small cereal) Weight: 300 g |
| Cereal box 2 | 27.5*16*5.4 cm (Large cereal) Weight: 1.35 kg |
| Screw bolt | 7*5*5 mm |
| Stone | 7*4*2 mm |

Figure 3:
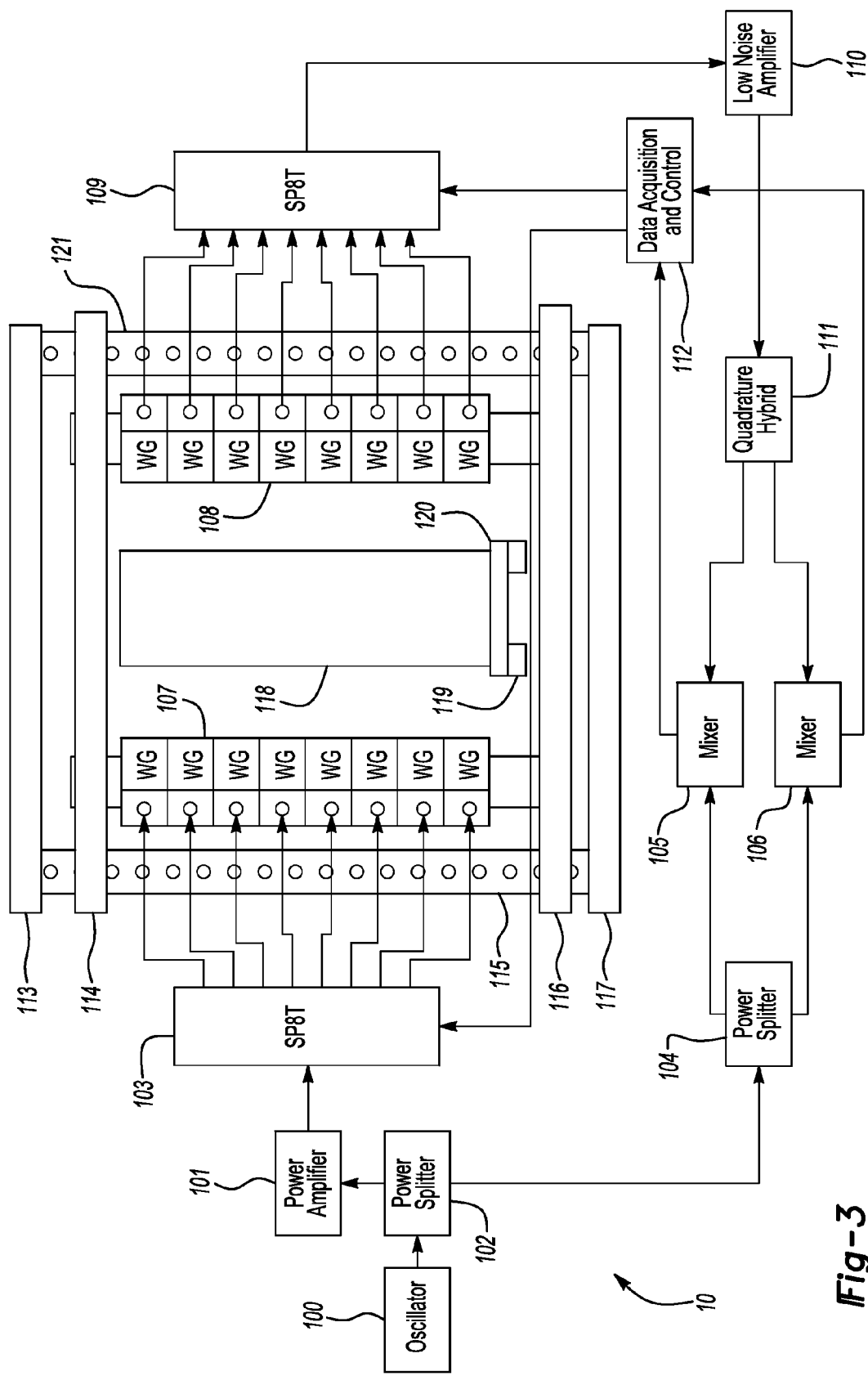
FIG. 3 is a schematic of the microwave system of FIG. 1.

According to the simulation results and the necessary calculation, we need to set up the transmitter and receiver. Both of them are controlled by a computer through a PC card. The basis of the equipment selection is these components have low noise figure, low insertion loss, low VSWR and reasonable price. FIG. 3 illustrates one system 10 constructed according to the invention and which can be used to detect the contaminant in the medium and image the target. The main equipment includes oscillator 100, mixers 105, 106, low noise amplifier 110, power amplifier 101, switch and the data acquisition system 112.

The proposed system utilizes the low-energy microwave technology and can be used to inspect the object 119. The system will be cost effective, safer, versatile and innovative compared to existing systems.

The system 10 is coherent and retains both phase and amplitude information of received signals. Variations due to differences in the transmit/receive channels are calibrated out by data processing. After data acquisition, the data is modified because the waveguide array 108 of system 10 collects the scattered signal of medium 118 in eight channels. Once the measurements are processed, the detection and imaging algorithm utilizes the modified data to obtain profiles of the electrical properties.

System 10 utilizes eight transmit channels and eight receive channels with the operation frequency of 15 GHz. The system 10 utilizes low cost, well-characterized microwave components to reduce system integration problems.

System 10 extracts both the real ("Q") and imaginary ("I") parts of the electrical properties of the medium 118. A continuous wave ("CW") signal of 15 GHz is emitted continuously from the oscillator 100 with the power level of 20 dBm. The signal then is split by a power splitter 102. One part of the signal is used the as the reference signal. The other part of the signal heads to the transmission array passing through a power amplifier 101. An eight-channel switch (SP8T) 103 is used for scanning control. The transmission array includes eight waveguides WR62 107 working as the transmitter. The received signal is fed into a 90 degree hybrid then compared with the original reference CW signal using two mixers 105 and 106. The resulting IF signals, including I and Q components, are sent to a data acquisition and control unit 112 which performs A/D conversions.

The mixer is design to mix the received signal with the source signal. The LO/RF is 6.0–18.0 GHz. The IF frequency is DC-1.0 GHz. The IF port is connected to the data acquisition and control unit through a feedthru, which is working as a low pass filter.

Both the low-noise amplifier 110 and the power amplifier are working at 14.5–15.3 GHz with the gain of 40 dB. They are used in the transmitter and receiver respectively to amplify the signal when it is not detectable by the data acquisition and control unit 112. An AD/DA card, the main component of the data acquisition and control unit 112, is needed to control the switches and data acquisition. It also provides the interface between the software and the hardware. In the system shown, a different switch velocity for Rx and Tx. Vr=8*Vt is used.

In FIG. 3, 113 to 117 are a rack designed to hold the arrays and attach them to a conveyer belt 121. Two pairs of horizontal and vertical panels are adjustable according to the dimension of the medium tested.

Figure 7:
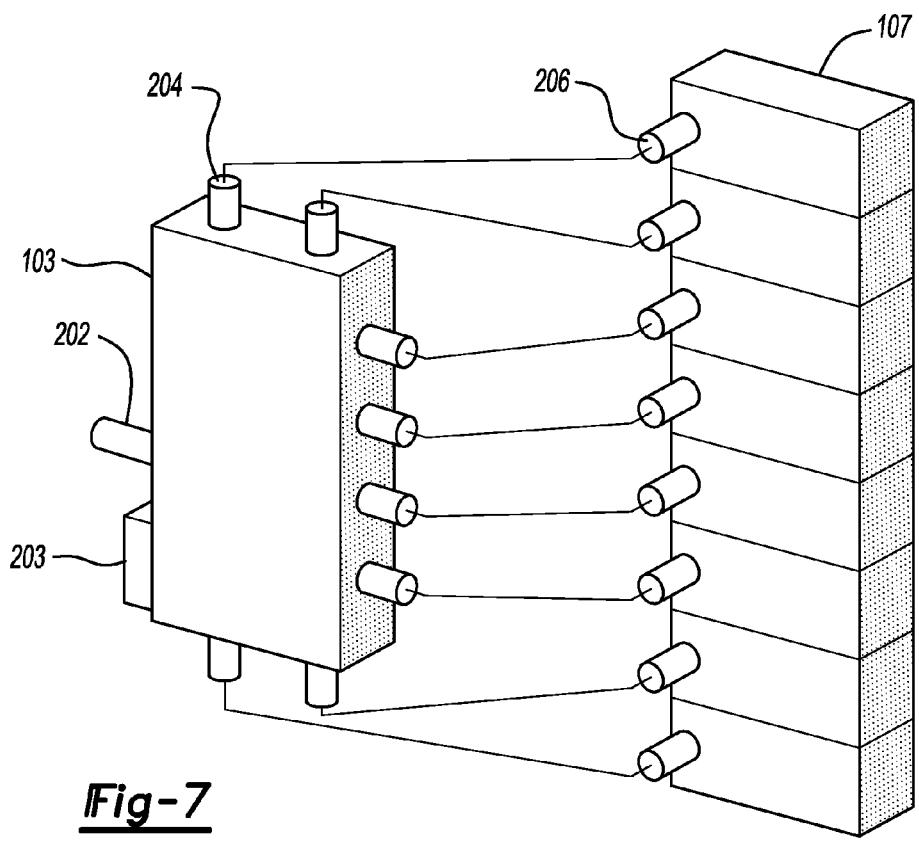
FIG. 7 illustrates a waveguide array with a switch that could be used in the system of FIG. 1.

The waveguide array pair 107, 108 can be spaced from each other with appropriate spacers and relative to the dimension of the medium 118. FIG. 7 illustrates one such arrangement, showing view of the waveguide array and the scanning control unit. As noted, a microwave switch SP8T 103 is connected to a waveguide array 107, which consists of eight waveguide WR62 by attaching one by one. A SMA adapter 202 is the input port of the switch 103 while other eight SMA adapters 204 are the output ports. An encoded TTL interface 203 is connect to the data acquisition and control unit which sends three digits code to control the eight channels on and off so that the microwave beam scans along the direction. Waveguides are used in this invention because of the good directional property and ease of integration.

Figure 8:
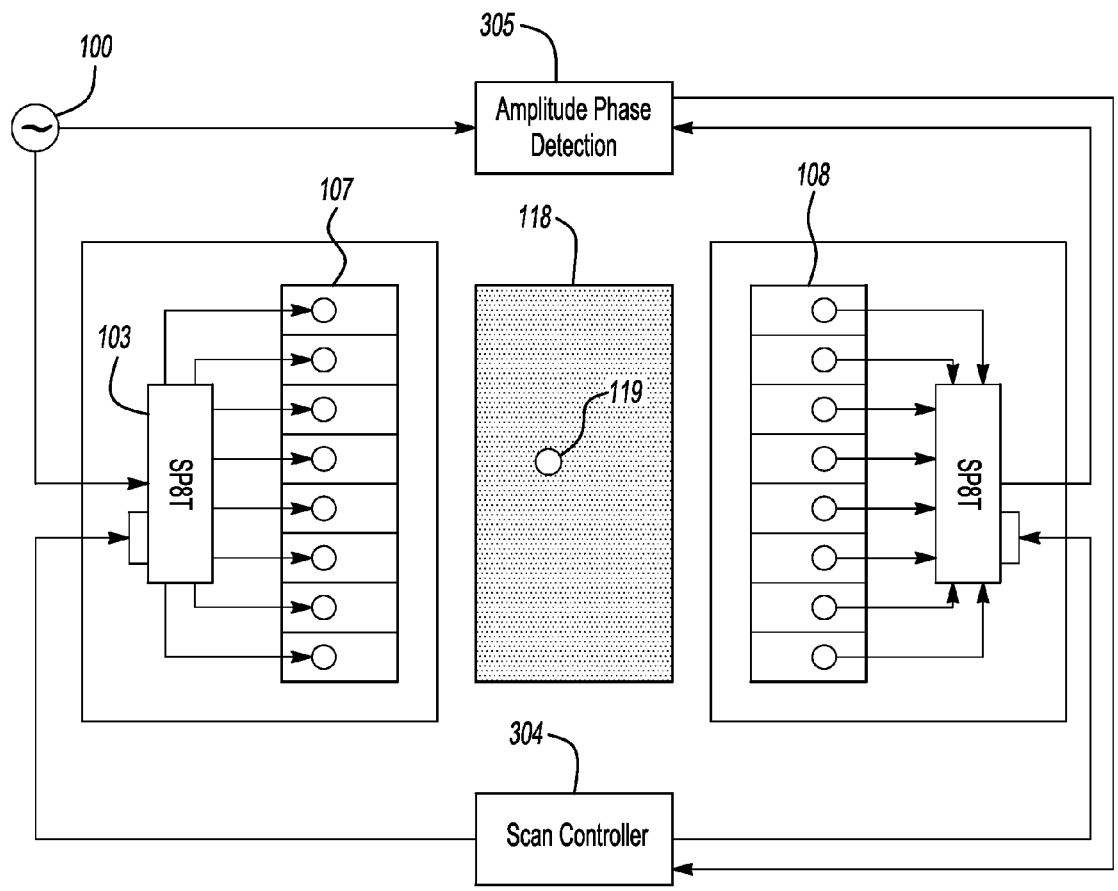
FIG. 8 is a schematic of an electrical control and scan scheme for the system of FIG. 1.
Figure 9:
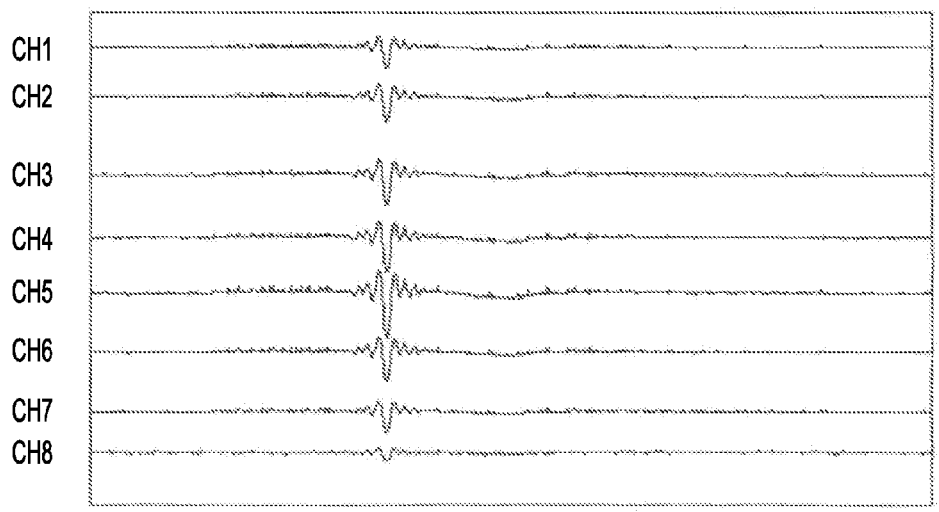
FIG. 9 illustrates signals which may be obtained in eight channels.

FIG. 8 shows the electrical control and scan scheme. The 15 GHz microwave signals generated by the oscillator 100 are sent to the transmitter waveguide array 107 and corresponding switch 103. The data acquisition and control unit switches the eight waveguides to transmit the microwave signal. When one of the waveguides is operating, the receiver array on the other side controls each one of the receiver waveguides to receive the scattered signal such that all the eight receiving waveguides work in turn when each transmitting waveguide is sending signal. FIG. 9 illustrates the signals, which may be received through eight different channels of the receiver waveguide array 108.

The description of the invention has been presented for purposes of illustration and description. It is not intended to be exhaustive or to limit the invention to the precise forms disclosed. Obvious modifications or variations are possible considering the above teachings. The cereal box were chosen and described to provide the best illustration of the principles of the invention and its practical applications to thereby enable one of ordinary skill in the art to utilize the invention in various media and with various modifications as are suited to the particular use contemplated.

What is claimed is:

1. A microwave system for inspecting a food product comprising:
   a first waveguide array transmitting a microwave through the food product;
   a second waveguide array receiving the microwave in a plurality of channels after passing through the food product; and
   a signal analyzer for analyzing a signal from the plurality of channels of the second waveguide array to inspect the food product.

2. The system of claim 1 further including a first switch for controlling the first waveguide array.

3. The system of claim 2 further including a second switch for controlling the second waveguide array.

4. The system of claim 3 wherein the signal analyzer extracts magnitude and phase information from the signal from the second waveguide array.

5. A method for inspecting a food product including the steps of:
   transmitting a microwave through the food product;
   receiving the microwave in a plurality of channels of a receiving waveguide array after it passes through the food product; and
   analyzing the received microwave to inspect the food product.

6. The method of claim 5 further including the steps of:
   generating a wave signal;
   generating the microwave in a plurality of channels of a transmitting waveguide array based upon the wave signal; and
   comparing the wave signal to the signal from the received microwave to inspect the food product.

7. The method of claim 6 further including the steps of extracting magnitude and phase information from the received microwave and analyzing the magnitude and phase information.

8. The method of claim 6 further including the step of mixing the wave signal and the signal from the received microwave in order to perform the step of comparing.

9. The method of claim 8 further including the step of detecting the presence of an object in the food product based upon the step of analyzing the received microwave.

10. The method of claim 5 further including the step of detecting the presence of an object in the food product based upon the step of analyzing the received microwave.

* * * * *